(12) United States Patent
Siebrecht et al.

(10) Patent No.: US 8,343,151 B2
(45) Date of Patent: Jan. 1, 2013

(54) VESSEL SEALER AND DIVIDER WITH CAPTURED CUTTING ELEMENT

(75) Inventors: Wayne Siebrecht, Golden, CO (US); Thomas J. Gerhardt, Jr., Littleton, CO (US); Larry Johnson, Bennett, CO (US); John J. Kappus, Denver, CO (US); Arlen J. Reschke, Longmont, CO (US)

(73) Assignee: Covidien LP, Mansfield, MA (US)

( * ) Notice: Subject to any disclaimer, the term of this patent is extended or adjusted under 35 U.S.C. 154(b) by 568 days.

(21) Appl. No.: 12/576,380

(22) Filed: Oct. 9, 2009

(65) Prior Publication Data

US 2011/0087221 A1   Apr. 14, 2011

(51) Int. Cl.
*A61B 18/14* (2006.01)
(52) U.S. Cl. .................................. 606/51; 606/45
(58) Field of Classification Search .............. 606/45, 606/50–52
See application file for complete search history.

(56) References Cited

U.S. PATENT DOCUMENTS

| | | | |
|---|---|---|---|
| 5,389,098 A | 2/1995 | Tsuruta et al. | |
| 5,509,922 A | 4/1996 | Aranyi et al. | |
| 5,573,535 A * | 11/1996 | Viklund | 606/51 |
| 5,582,611 A * | 12/1996 | Tsuruta et al. | 606/46 |
| 5,674,220 A | 10/1997 | Fox et al. | |
| 5,688,270 A | 11/1997 | Yates et al. | |
| 5,693,051 A | 12/1997 | Schulze et al. | |
| 5,797,938 A | 8/1998 | Paraschac et al. | |
| 7,101,371 B2 | 9/2006 | Dycus et al. | |
| 7,887,536 B2 | 2/2011 | Johnson et al. | |
| 8,016,827 B2 | 9/2011 | Chojin | |
| 8,112,871 B2 | 2/2012 | Brandt et al. | |
| 8,114,122 B2 | 2/2012 | Nau, Jr. | |
| 8,133,254 B2 | 3/2012 | Dumbauld et al. | |
| 8,142,473 B2 | 3/2012 | Cunningham | |
| 8,162,965 B2 | 4/2012 | Reschke et al. | |
| 8,162,973 B2 | 4/2012 | Cunningham | |
| 2005/0096651 A1* | 5/2005 | Truckai et al. | 606/51 |
| 2008/0021450 A1 | 1/2008 | Couture | |
| 2010/0016857 A1 | 1/2010 | McKenna et al. | |

(Continued)

FOREIGN PATENT DOCUMENTS

DE          2415263          10/1975

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner* — Micheal Peffley

(57) ABSTRACT

A forceps includes a housing having a shaft extending therefrom. The shaft has an end effector assembly that defines a longitudinal axis therethrough. The end effector assembly includes first and second jaw members disposed in opposed relation and moveable from a first, open position to a second, closed position for grasping tissue therebetween and a knife. One or more jaw members include knife blade channels defined therein. Each knife blade channel includes a polygonal longitudinal cross-section defined therein. The knife includes a knife edge and a knife base. The knife base includes a corresponding polygonal longitudinal cross-section. The knife is configured to translate through the knife blade channels and the knife base is configured to slidingly engage the knife base channel having the polygonal cross section upon translation of the knife. In embodiments, the knife blade channel and the knife base have a T-shaped longitudinal cross-section.

18 Claims, 11 Drawing Sheets

U.S. PATENT DOCUMENTS

| | | |
|---|---|---|
| 2010/0023009 A1 | 1/2010 | Moses et al. |
| 2010/0036375 A1 | 2/2010 | Regadas |
| 2010/0042140 A1 | 2/2010 | Cunningham |
| 2010/0042143 A1 | 2/2010 | Cunningham |
| 2010/0049187 A1 | 2/2010 | Carlton et al. |
| 2010/0057081 A1 | 3/2010 | Hanna |
| 2010/0057082 A1 | 3/2010 | Hanna |
| 2010/0057083 A1 | 3/2010 | Hanna |
| 2010/0057084 A1 | 3/2010 | Hanna |
| 2010/0063500 A1 | 3/2010 | Muszala |
| 2010/0069903 A1 | 3/2010 | Allen, IV et al. |
| 2010/0069904 A1 | 3/2010 | Cunningham |
| 2010/0069953 A1 | 3/2010 | Cunningham et al. |
| 2010/0076427 A1 | 3/2010 | Heard |
| 2010/0076430 A1 | 3/2010 | Romero |
| 2010/0076431 A1 | 3/2010 | Allen, IV |
| 2010/0076432 A1 | 3/2010 | Horner |
| 2010/0087816 A1 | 4/2010 | Roy |
| 2010/0094287 A1 | 4/2010 | Cunningham et al. |
| 2010/0100122 A1 | 4/2010 | Hinton |
| 2010/0145334 A1 | 6/2010 | Olson et al. |
| 2010/0179545 A1 | 7/2010 | Twomey et al. |
| 2010/0179546 A1 | 7/2010 | Cunningham |
| 2010/0179547 A1 | 7/2010 | Cunningham et al. |
| 2010/0249769 A1 | 9/2010 | Nau, Jr. et al. |
| 2010/0249776 A1 | 9/2010 | Kerr |
| 2010/0256635 A1 | 10/2010 | McKenna et al. |
| 2010/0274244 A1 | 10/2010 | Heard |
| 2010/0280511 A1 | 11/2010 | Rachlin et al. |
| 2011/0015632 A1 | 1/2011 | Artale |
| 2011/0034918 A1 | 2/2011 | Reschke |
| 2011/0054467 A1 | 3/2011 | Mueller et al. |
| 2011/0054468 A1 | 3/2011 | Dycus |
| 2011/0054469 A1 | 3/2011 | Kappus et al. |
| 2011/0054471 A1 | 3/2011 | Gerhardt et al. |
| 2011/0054472 A1 | 3/2011 | Romero |
| 2011/0060333 A1 | 3/2011 | Mueller |
| 2011/0060334 A1 | 3/2011 | Brandt et al. |
| 2011/0060335 A1 | 3/2011 | Harper et al. |
| 2011/0071523 A1 | 3/2011 | Dickhans |
| 2011/0072638 A1 | 3/2011 | Brandt et al. |
| 2011/0077648 A1 | 3/2011 | Lee et al. |
| 2011/0077649 A1 | 3/2011 | Kingsley |
| 2011/0082457 A1 | 4/2011 | Kerr et al. |
| 2011/0082494 A1 | 4/2011 | Kerr et al. |
| 2011/0087221 A1 | 4/2011 | Siebrecht et al. |
| 2011/0098689 A1 | 4/2011 | Nau, Jr. et al. |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 19738457 | 1/2009 |
| EP | 1159926 | 12/2001 |
| EP | 1810625 | 8/2009 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; Vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001.

Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 003813.4 dated Aug. 3, 2009.
Int'l Search Report EP 09 004491.8 dated Sep. 9, 2009.
Int'l Search Report EP 09 005575.7 dated Sep. 9, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

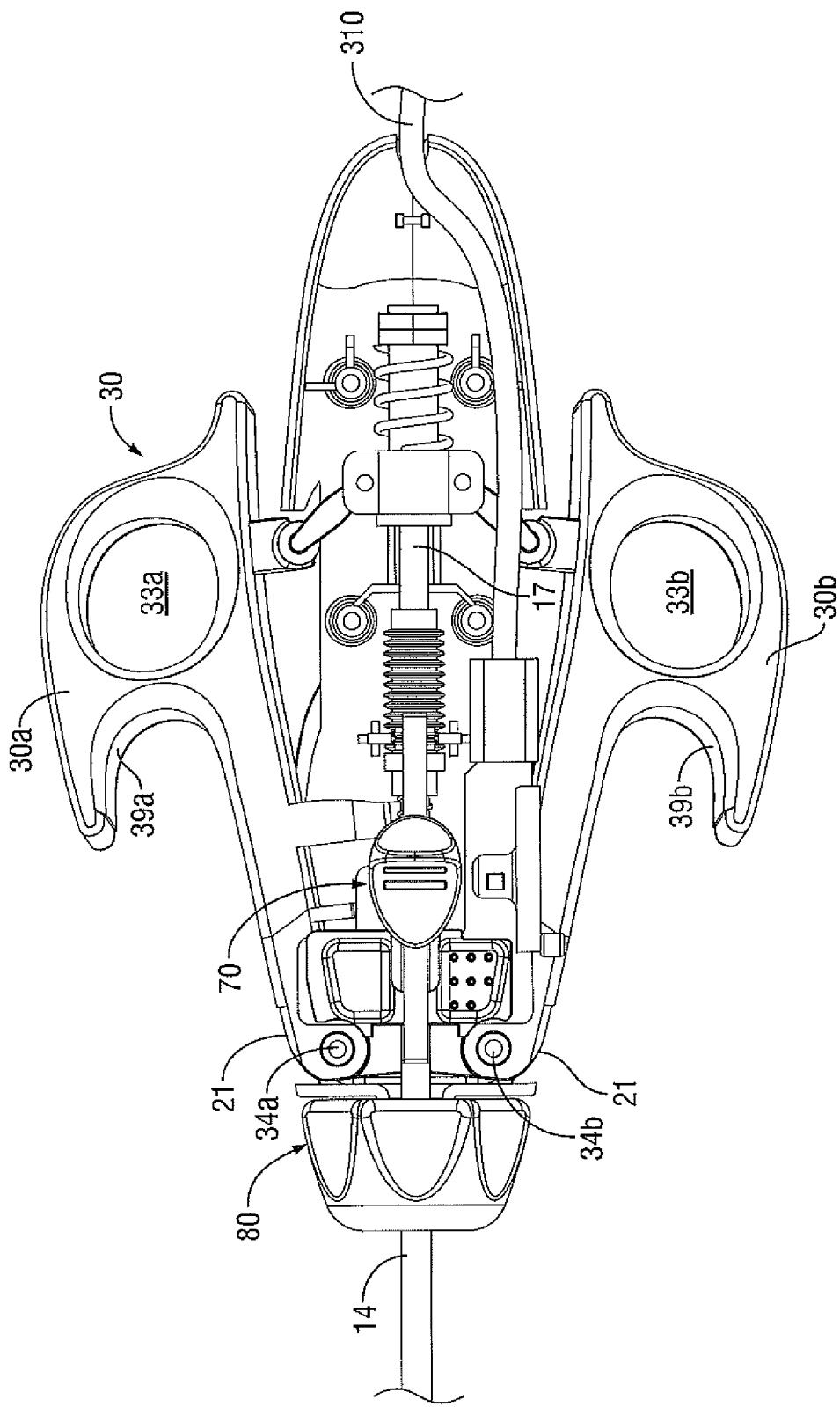

VESSEL SEALER AND DIVIDER WITH CAPTURED CUTTING ELEMENT

BACKGROUND

1. Technical Field

The present disclosure relates to an apparatus for performing an endoscopic electrosurgical procedure. More particularly, the present disclosure relates to an apparatus for performing an endoscopic electrosurgical procedure that employs an endoscopic electrosurgical apparatus that includes an end effector assembly configured for use with variously-sized access ports.

2. Description of Related Art

Electrosurgical apparatuses (e.g., electrosurgical forceps) are well known in the medical arts and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect hemostasis by heating the tissue and blood vessels to coagulate, cauterize, seal, cut, desiccate, and/or fulgurate tissue.

As an alternative to open electrosurgical forceps for use with open surgical procedures, many modern surgeons use endoscopes and endoscopic electrosurgical apparatuses (e.g., endoscopic forceps, laparoscopic forceps) for remotely accessing organs through smaller, puncture-like incisions. As a direct result thereof, patients tend to benefit from less scarring and reduced healing time. Typically, the endoscopic forceps is inserted into the patient through one or more various types of cannulas or access ports (typically having an opening that ranges from about five millimeters to about twelve millimeters) that has been made with a trocar; as can be appreciated, smaller cannulas are usually preferred.

An endoscopic forceps that is configured for use with small cannulas (e.g., cannulas less than five millimeters) may present design challenges for a manufacturer of endoscopic instruments.

SUMMARY

The present disclosure relates to a forceps including a housing having a shaft extending therefrom. The shaft has an end effector assembly disposed at a distal end thereof. The end effector assembly defines a longitudinal axis therethrough and includes a first jaw member, a second jaw member, and a knife.

The first and second jaw members are disposed in opposed relation and are moveable from a first, open position to a second, closed position for grasping tissue therebetween. One or more of the jaw members may be adapted to connect to an electrosurgical energy source to communicate energy to tissue disposed between the jaw members. The jaw members may be curved. The jaw members include knife blade channels defined therein. One or more of the knife blade channels may include a polygonal longitudinal cross-section defined therein. In embodiments, the distal portions of the knife blade channels may be curved.

The knife includes a knife edge and a knife base. The knife edge may be disposed substantially perpendicular to the knife base. The knife edge may be disposed in vertical registration with the knife base. The knife base may include a polygonal longitudinal cross-section corresponding to the one or more knife blade channels having a polygonal longitudinal cross-section. The polygonal cross-section of one or more of the knife blade channels is dimensioned to capture the knife base therein to prevent the knife from escaping each respective knife blade channel having the polygonal longitudinal cross-section upon distal translation thereof. The knife is configured to translate through the knife blade channels and the knife base is configured to slidingly engage the one or more knife blade channels having the polygonal longitudinal cross sections upon translation of the knife.

In one embodiment, one or more knife blade channels define a rectangular cross-section therein and the knife base defines a corresponding rectangular cross-section. The knife base may include a full radii curved distal tip. A portion of one or more knife blade channels may be dimensioned to have a width that is less than the width of the one or more respective remaining knife blade channels to secure and retain the knife base therein.

In another embodiment according to the present disclosure, the forceps includes a housing having a shaft extending therefrom. The shaft has an end effector assembly disposed at a distal end thereof. The end effector assembly defines a longitudinal axis therethrough and includes a first jaw member, a second jaw member, and a knife.

The first and second jaw members are disposed in opposed relation and are moveable from a first, open position to a second, closed position for grasping tissue therebetween. One or more of the jaw members may be adapted to connect to an electrosurgical energy source to communicate energy to tissue disposed between the jaw members. The jaw members may be curved. The jaw members include knife blade channels defined therein. One or more of the knife blade channels includes a T-shaped, longitudinal cross-section defined therein. In embodiments, the distal portions of the knife blade channels may be curved.

The knife includes a knife edge and a knife base. The knife edge may be disposed substantially perpendicular to the knife base. The knife edge may be disposed in vertical registration with the knife base. The knife base may include a T-shaped, longitudinal cross-section corresponding to the one or more knife blade channels having a T-shaped, longitudinal cross-section. The T-shaped, longitudinal cross-section of one or more of the knife blade channels is dimensioned to capture the knife base therein to prevent the knife from escaping each respective knife blade channel having the T-shaped, longitudinal cross-section upon distal translation thereof. The knife is configured to translate through the knife blade channels and the knife base is configured to slidingly engage the one or more knife blade channels having the T-shaped, longitudinal cross sections upon translation of the knife.

The knife base may include a full radii curved distal tip. A portion of one or more knife blade channels may be dimensioned to have a width that is less than the width of the one or more respective remaining knife blade channels to secure and retain the knife base therein.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2A is an enlarged, top view of the forceps of FIG. 1A showing the disposition of the internal components when the forceps is in an open configuration;

DETAILED DESCRIPTION

Detailed embodiments of the present disclosure are disclosed herein; however, the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful to provide an electrosurgical apparatus that is suitable for use with various access ports, including but not limited to those that are greater than and/or less than five millimeters. With this purpose in mind, the present disclosure includes an electrosurgical forceps that includes a drive assembly operatively coupled to one or more jaw members associated with the end effector assembly of the electrosurgical forceps. The drive assembly is configured to move the jaws from an open to a closed configuration that forms a closed loop electrical circuit such that a desired tissue effect (e.g., a tissue seal) may be achieved.

Figure 1A:
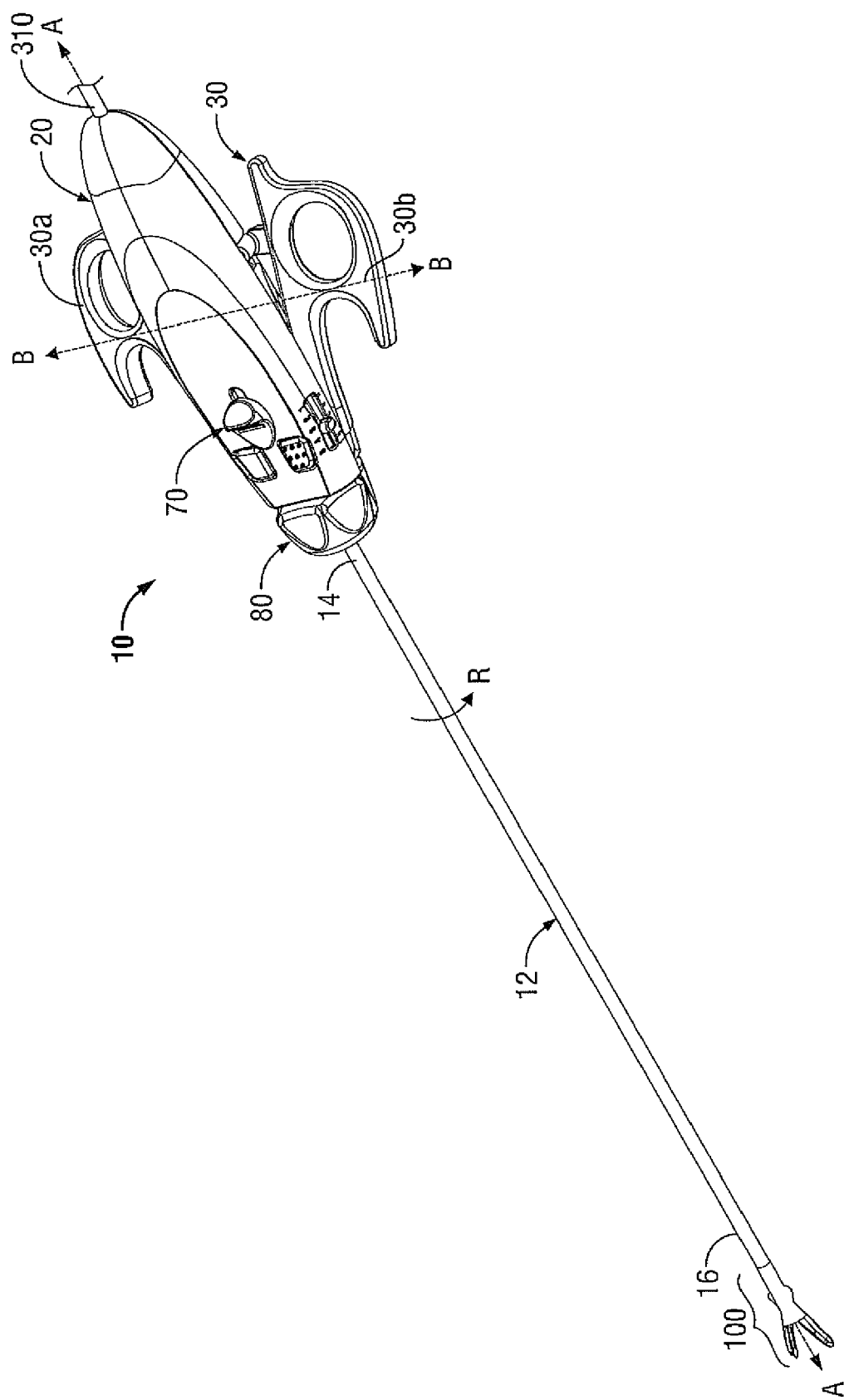
FIG. 1A is a top, perspective view of an endoscopic forceps shown in an open configuration and including a housing, a handle assembly, a shaft and an end effector assembly according to the present disclosure.
Figure 1B:
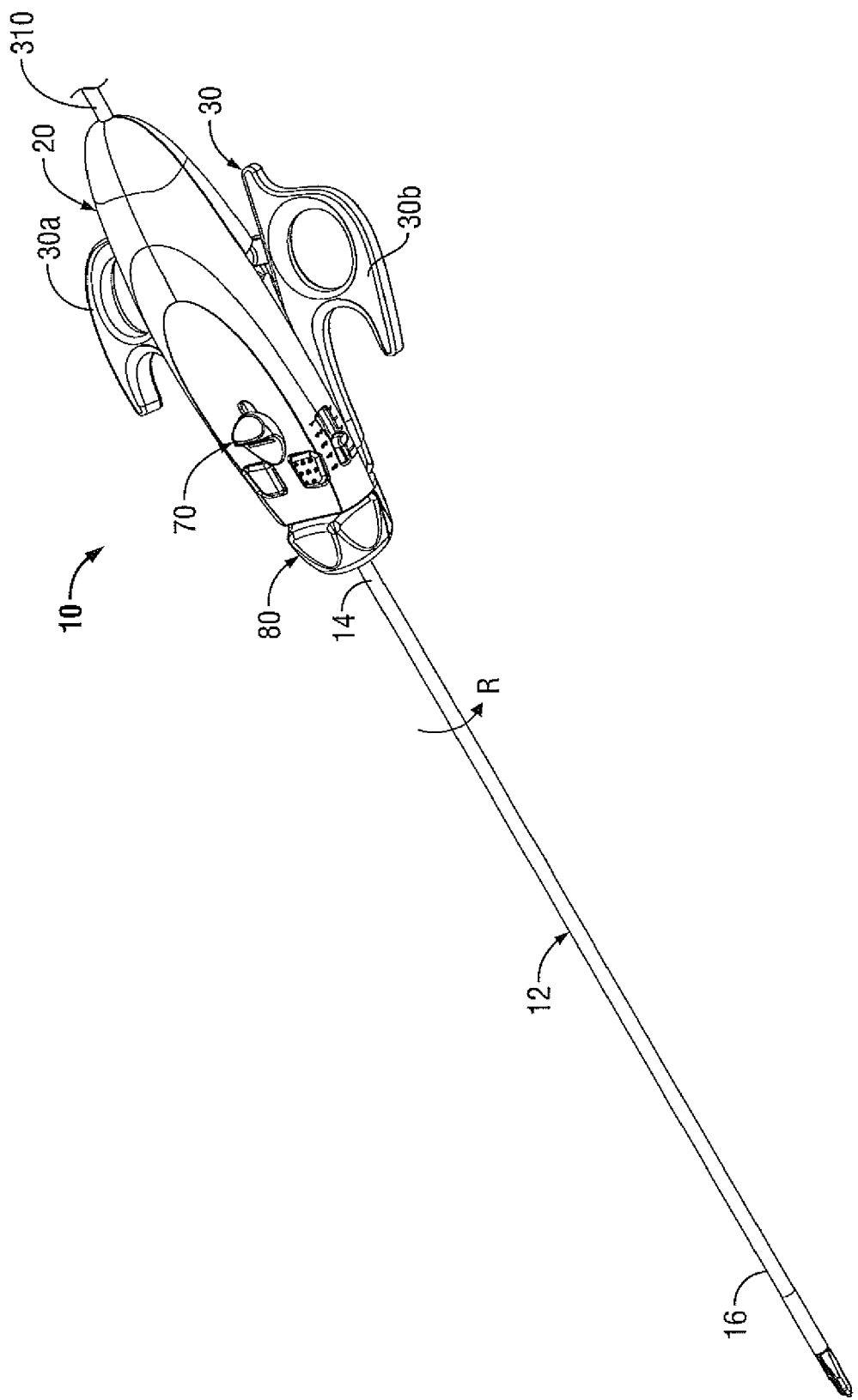
FIG. 1B is a top, perspective view of the endoscopic forceps of FIG. 1A showing the end effector assembly in a closed configuration according to the present disclosure.

Turning now to FIGS. 1A and 1B, one embodiment of an endoscopic electrosurgical forceps 10 is shown for use with various surgical procedures and generally includes a housing 20, a handle assembly 30, a rotating assembly 80, a knife trigger assembly 70 and an end effector assembly 100 which mutually cooperate to grasp, seal and divide tubular vessels and vascular tissue. Although the majority of the figure drawings depict a forceps 10 for use in connection with endoscopic surgical procedures, the present disclosure may be used for more traditional open surgical procedures. For the purposes herein, the forceps 10 is described in terms of an endoscopic instrument; however, it is contemplated that an open version of the forceps may also include the same or similar operating components and features as described below.

Forceps 10 includes a shaft 12 which has a distal end 16 dimensioned to mechanically engage the end effector assembly 100 and a proximal end 14 which mechanically engages the housing 20. Details of how the shaft 12 connects to the end effector assembly 100 are described in more detail below. The proximal end 14 of shaft 12 is received within the housing 20 and the connections relating thereto are also described in detail below. In the drawings and in the descriptions which follow, the term "proximal", as is traditional, will refer to the end of the forceps 10 which is closer to the user, while the term "distal" will refer to the end which is farther from the user.

Forceps 10 also includes an electrosurgical cable 310 that may connect the forceps 10 to a source of electrosurgical energy, e.g., a generator. Generators such as those sold by Covidien's Energy-based Devices global business unit, located in Boulder, Colo. may be used as a source of both bipolar electrosurgical energy for sealing vessels and vascular tissues as well as monopolar electrosurgical energy which is typically employed to coagulate or cauterize tissue. It is envisioned that the generator may include various safety and performance features including isolated output, impedance control and/or independent actuation of accessories.

Handle assembly 30 includes two movable handles 30a and 30b disposed on opposite sides of housing 20. Handles 30a and 30b are movable relative to one another to actuate the end effector assembly 100 as explained in more detail below with respect to the operation of the jaws 10.

Rotating assembly 80 is mechanically coupled to housing 20 and is rotatable approximately 90 degrees in either direction about a longitudinal axis "A." Rotating assembly 80, when rotated, rotates shaft 12, which, in turn, rotates end effector assembly 100. Such a configuration allows end effector assembly 100 to be rotated approximately 90 degrees in either direction with respect to housing 20.

As mentioned above, end effector assembly 100 is attached at the distal end 16 of shaft 12 and includes a pair of opposing jaw members 110 and 120 (see FIG. 6). Handles 30a and 30b of handle assembly 30 ultimately connect to drive assembly 60 (see FIG. 2A) which, together, mechanically cooperate to impart movement of the jaw members 110 and 120 from a first, open position wherein the jaw members 110 and 120 are disposed in spaced relation relative to one another, to a second, clamping or closed position wherein the jaw members 110 and 120 cooperate to grasp tissue therebetween.

Turning now to the more detailed features of the present disclosure as described with respect to FIGS. 1A-7B, handles 30a and 30b each include an aperture 33a and 33b, respectively, defined therein which enables a user to grasp and move each respective handle 30a and 30b relative to one another. Handles 30a and 30b also include ergonomically-enhanced gripping elements 39a and 39b, respectively, disposed along an outer edge thereof which are designed to facilitate gripping of the handles 30a and 30b during actuation. It is envisioned that gripping elements 39a and 39b may include one or more protuberances, scallops and/or ribs to enhance gripping.

As best illustrated in FIG. 1A, handles 30a and 30b are configured to extend outwardly on opposite sides from a transverse axis "B" defined through housing 20 which is perpendicular to longitudinal axis "A". Handles 30a and 30b are movable relative to one another in a direction parallel to axis "B" to open and close the jaw members 110 and 120 as needed during surgery. Details relating to the inner-working components of forces 10 are disclosed in commonly-owned U.S. patent application Ser. No. 11/540,335. This forceps style is commonly referred to as an "in-line" or hemostat style forceps.

Figure 2B:
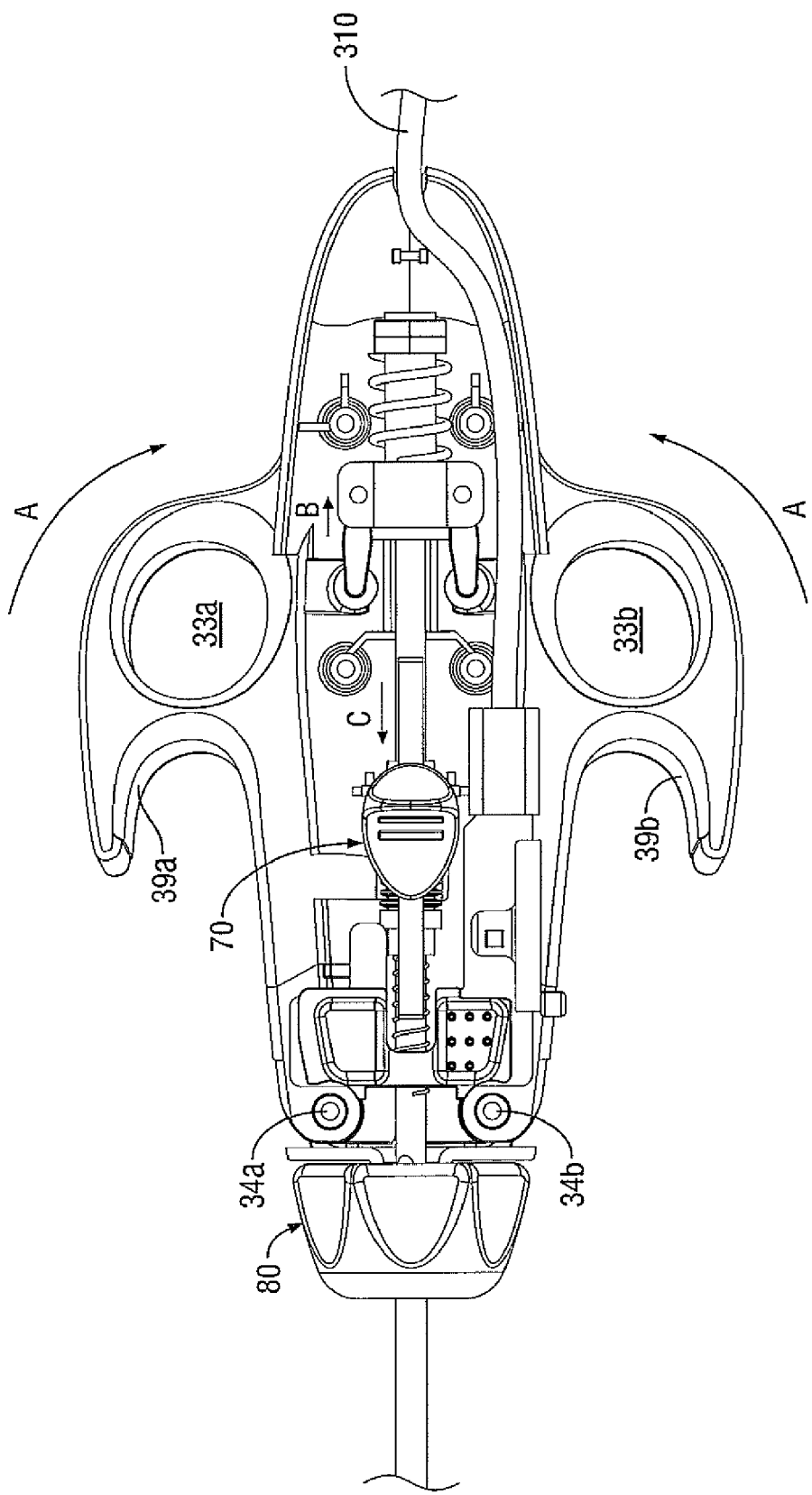
FIG. 2B is an enlarged, top view of the forceps of FIG. 1B showing the disposition of the internal components when the forceps is in a closed configuration.
Figure 3A:
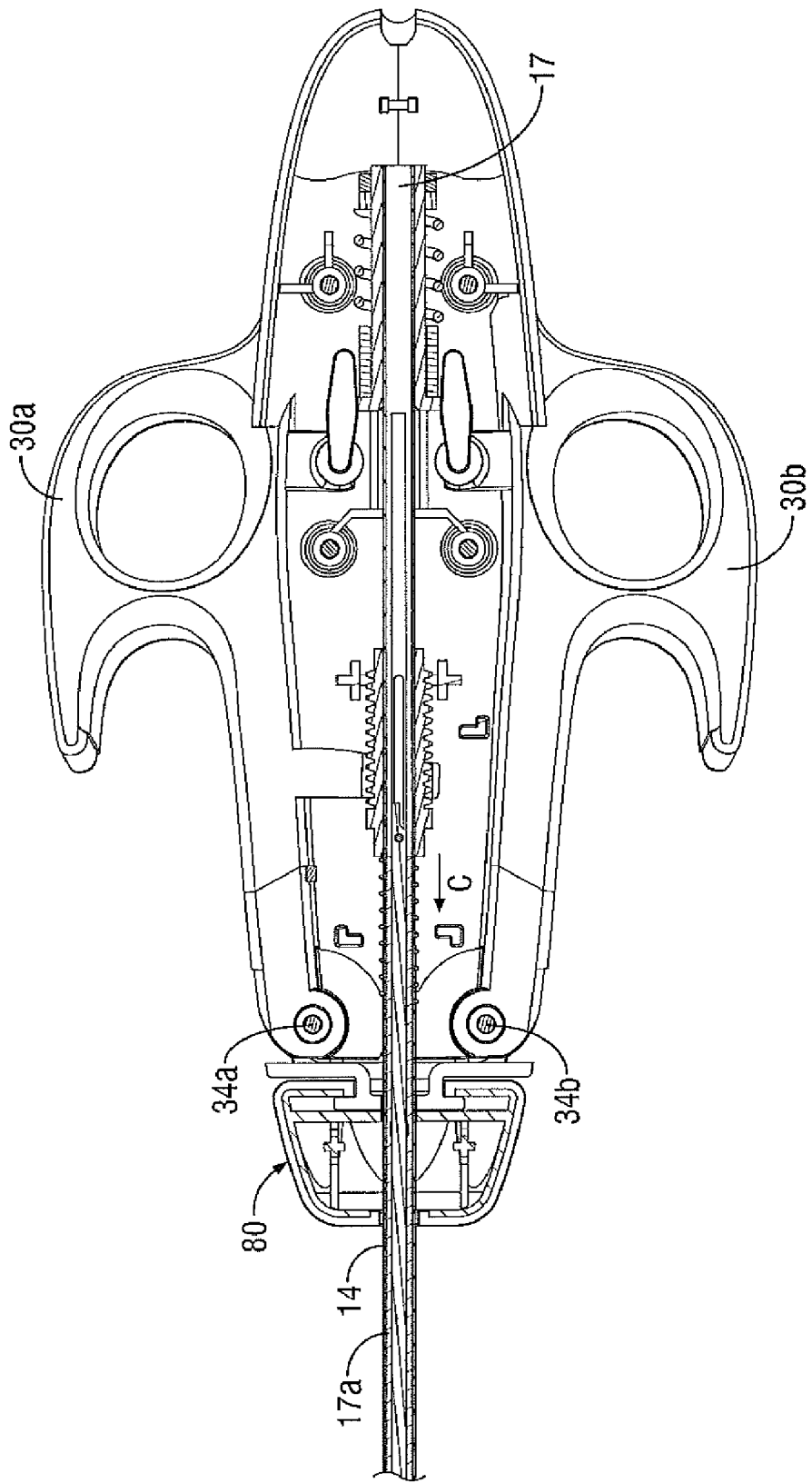
FIG. 3A is an enlarged, top view showing the knife actuator after actuation.
Figure 3B:
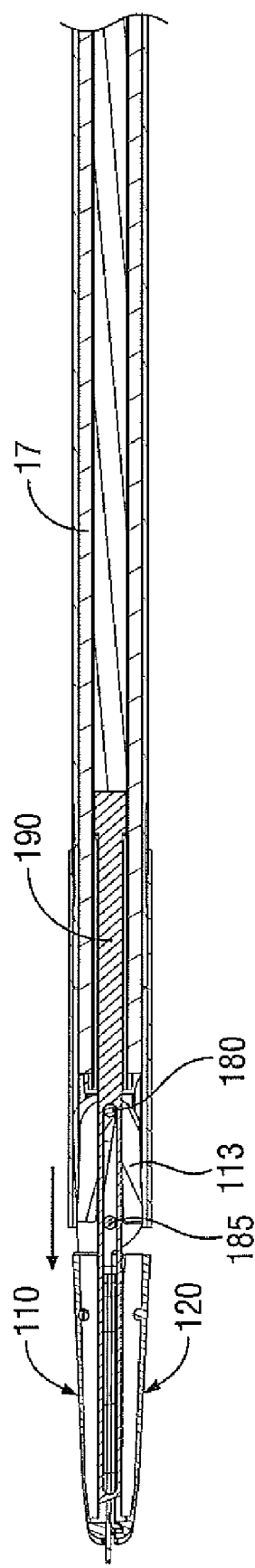
FIG. 3B is a greatly-enlarged, side cross sectional view of the end effector assembly showing the position of the knife after actuation.

As best seen in FIGS. 2A and 2B, the distal end of each handle 30a and 30b is selectively moveable about pivot pins 34a and 34b attached to a distal end 21 of the housing 20 to actuate the jaw members 110 and 120. Movement of the handles 30a and 30b away from one another (and the housing 20) unlocks and opens the handles 30a and 30b and, in turn, the jaw members 110 and 120 for subsequent grasping or re-grasping of tissue. In one embodiment, the handles 30a and 30b may be biased in an open configuration to facilitate handling and manipulation of the jaws within an operative field. Various spring-like mechanisms are contemplated which may be utilized to accomplish this purpose.

Movable handles 30a and 30b are designed to provide a distinct lever-like mechanical advantage over conventional handle assemblies. The enhanced mechanical advantage for actuating the jaw members 110 and 120 is gained by virtue of the unique position and combination of several inter-cooperating elements which reduce the overall user forces necessary to obtain and maintain the jaw members 110 and 120 under ideal operating pressures of about 3 kg/cm$^2$ to about 16 kg/cm$^2$. Details relating to the working components the handle assembly and drive assembly are disclosed in above-mentioned U.S. patent application Ser. No. 11/540,335. In other words, it is envisioned that the combination of these elements and their positions relative to one another enables the user to gain lever-like mechanical advantage to actuate the jaw members 110 and 120 enabling the user to close the jaw members 110 and 120 with lesser force while still generating the required forces necessary to effect a proper and effective tissue seal.

Figure 4A:
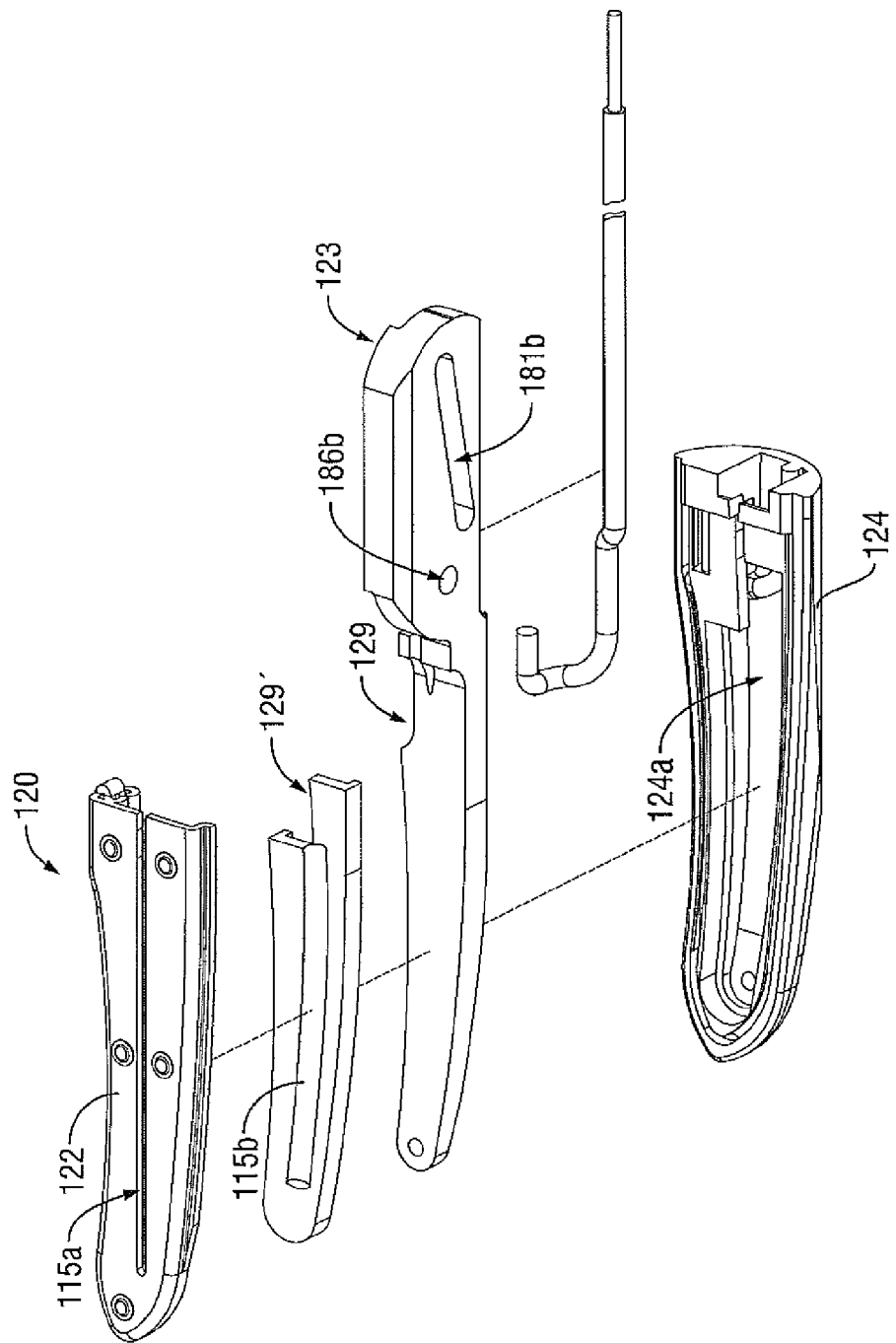
FIG. 4A is a greatly-enlarged, perspective view of the bottom jaw of the end effector assembly with parts separated.
Figure 4B:
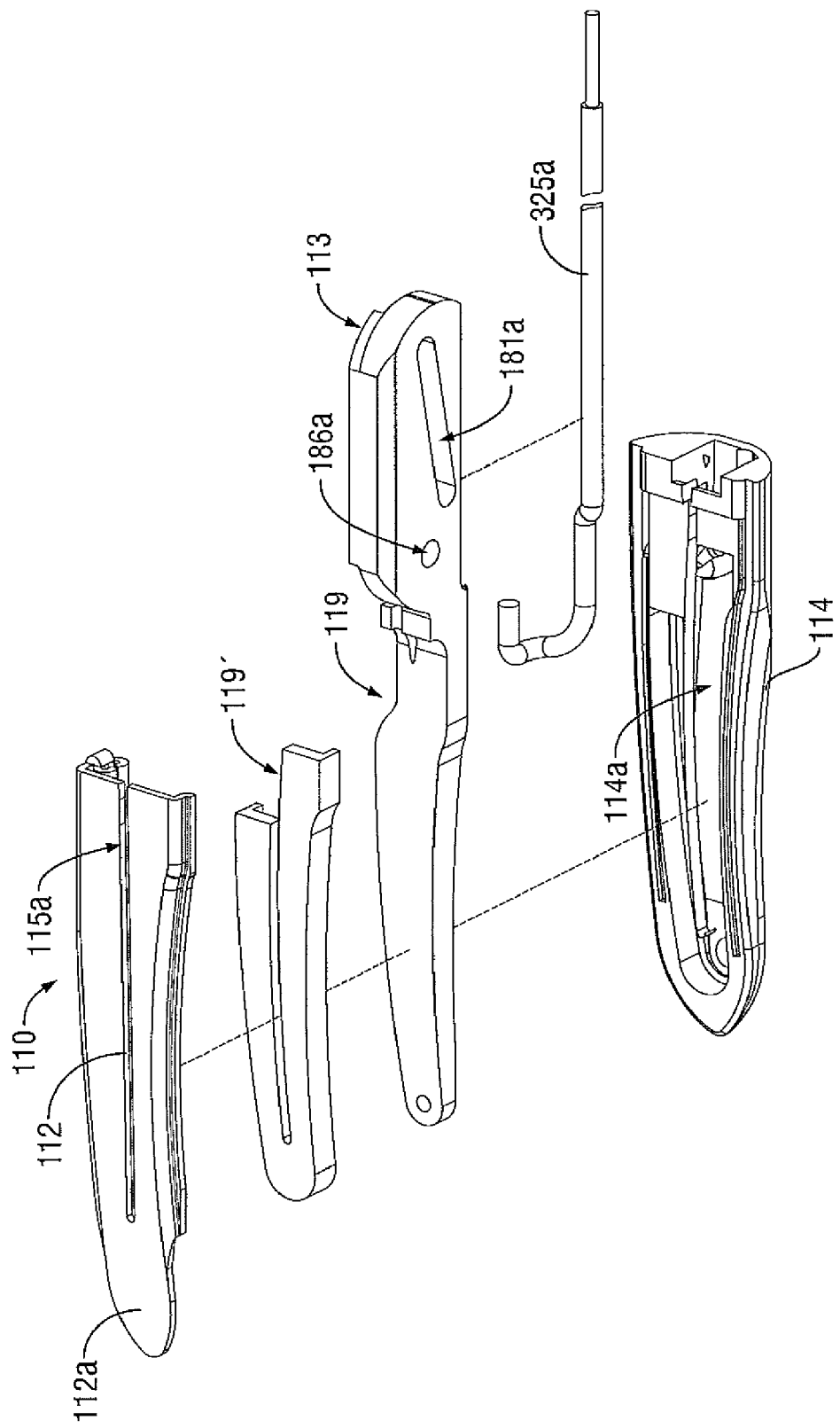
FIG. 4B is a greatly-enlarged, perspective view of the top jaw of the end effector assembly with parts separated.
Figure 5:
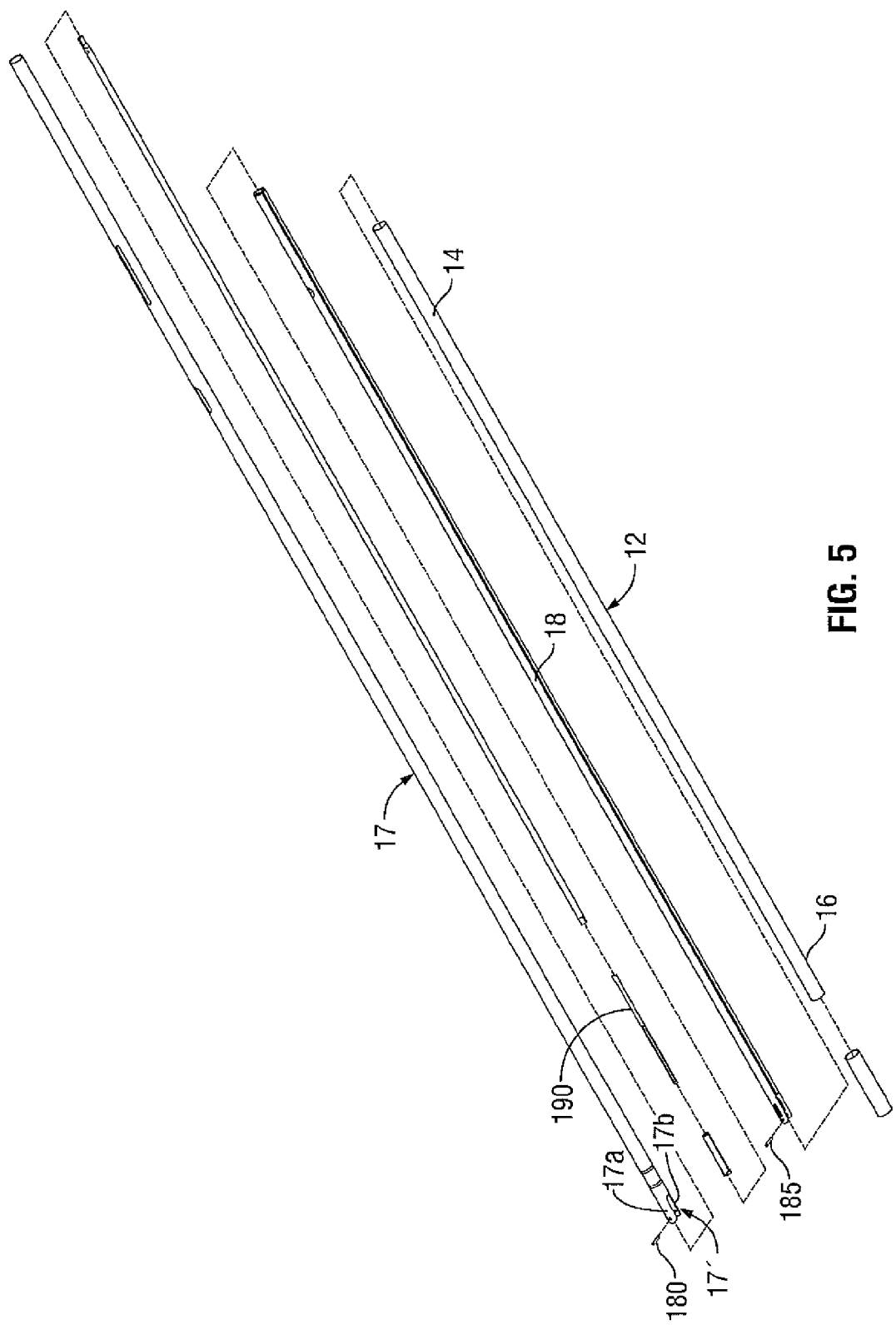
FIG. 5 is a greatly-enlarged, perspective view of the elongated shaft for housing various moving parts of the drive assembly and knife assembly.

As shown best in FIGS. 4A, 4B and 5, the end effector assembly 100 is designed as a bilateral assembly, e.g., both jaw members 110 and 120 pivot relative to one another about a pivot pin 185 disposed therethrough. More particularly, jaw members 110 and 120 include proximal flanges 113 and 123, respectively, which each include an elongated angled slot 181a and 181b, respectively, defined therethrough. Drive pin 180 mounts jaw members 110 and 120 to an end of a rotating shaft 18 and within a cavity 17' defined at the distal ends 17a and 17b of drive actuator or sleeve 17 (See FIG. 5). It should be noted that the teachings of the present invention may also be associated with a unilateral end effector assembly.

Upon actuation of the drive assembly 60, the drive sleeve 17 reciprocates which, in turn, causes the drive pin 180 to ride within slots 181a and 181b to open and close the jaw members 110 and 120 as desired. The jaw members 110 and 120, in turn, pivot about pivot pin 185 disposed through respective pivot holes 186a and 186b defined within flanges 113 and 123. As can be appreciated, squeezing handles 30a and 30b toward the housing 20 pulls drive sleeve 17 and drive pin 180 proximally to close the jaw members 110 and 120 about tissue grasped therebetween and pushing the sleeve 17 distally opens the jaw members 110 and 120 for grasping purposes.

End effector assembly 100 also houses a distal portion of knife 190 for translation therethrough. Upon actuation, and when jaw members 110 and 120 are disposed in the second position grasping tissue therebetween, knife 190 is translated distally from the shaft 12 through a knife channel 115a defined within jaw members 110 and 120, thereby cutting sealed tissue. Unique features relating to the knife and knife channels will be described in more detail below.

As best shown in FIG. 4A, jaw member 120 includes a support base 129 that extends distally from flange 123 and that is configured to support an insulative substrate 129' thereon. Insulative substrate 129', in turn, is configured to support an electrically conductive tissue engaging surface or sealing plate 122 thereon. Sealing plate 122 may be affixed atop the insulative substrate 129' and support base 129 in any known manner in the art, snap-fit, over-molding, stamping, ultrasonically welded, etc. Support base 129 together with the insulative substrate 129' and electrically conductive tissue engaging surface 122 are encapsulated by an outer insulative housing 124. Outer housing 124 includes a cavity 124a that is dimensioned to securely engage the electrically conductive sealing surface 122 as well as the support base 129 and insulative substrate 129'. This may be accomplished by stamping, by overmolding, by overmolding a stamped electrically conductive sealing plate and/or by overmolding a metal injection molded seal plate. All of these manufacturing techniques produce jaw member 120 having an electrically conductive surface 122, which is substantially surrounded by insulating materials. It should be noted that in other embodiments, jaw member 120 may be monolithic and formed from one solid material, such as a metal.

Figure 6A:
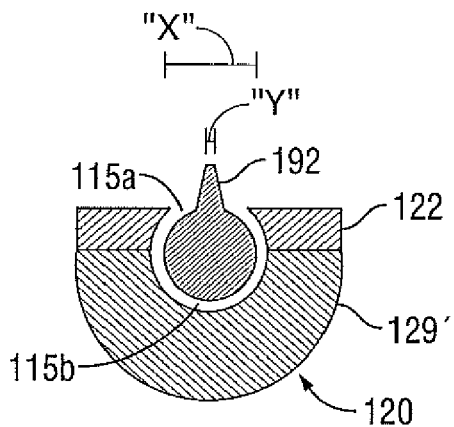
FIG. 6A is a rear view of one of the jaw members in which a base of the knife is disposed within a captured mount.

With reference now to FIGS. 4A and 6A, the electrically conductive surface or sealing plate 122 defines a longitudinally-oriented knife blade channel 115a therethrough for reciprocation of the knife 190. Insulative substrate 129' also includes a longitudinally-oriented channel, knife base channel 115b defined therethrough. As discussed above, sealing plate 122 is affixed atop insulative substrate 129 and is configured such that knife base channel 115b is disposed below and in vertical registration with knife blade channel 115a (see FIG. 6A). As shown in FIG. 6A, the width "X" of knife base channel 115b is greater than the width "Y" of knife blade channel 115a and the advantages of such will become readily apparent below. In the embodiment of FIG. 6A, knife base channel 115b has a circular cross-section, although other embodiments, (e.g., polygonal, T-shaped, L-shaped, etc.) as will be described below are also contemplated.

Figure 6B:
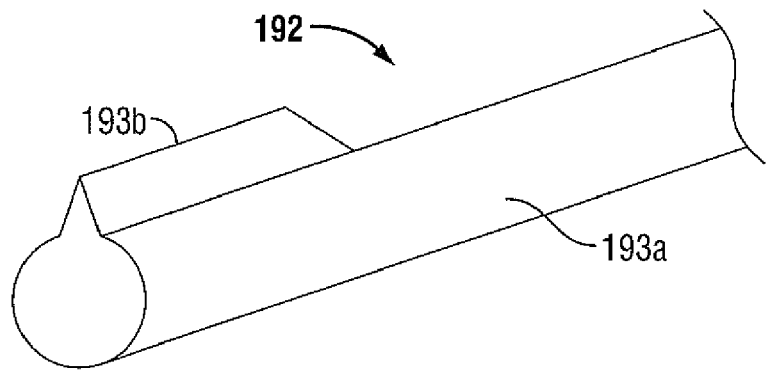
FIG. 6B is a perspective view of a distal end of a knife according to one embodiment of the present disclosure.

As shown in FIG. 6B, which depicts the distal end of knife 192, knife 192 includes a knife base 193a and a knife blade 193b. Knife blade 193b is disposed on top of knife base 193a and positioned toward a distal end thereof. Knife 192 is configured for use with jaw member 120 depicted in FIG. 6A, as will be described in more detail below. Knife base 193a is substantially similar in shape to knife base channel 115b defined within insulative substrate 129'. As can be appreciated, in the illustrated embodiment, a diameter of cylindrical knife base 193a is slightly less than a diameter of knife base channel 115b such that, upon deployment, knife base 193a may translate at least partially through knife base channel 115b. Similarly, knife blade 193b has a width that is smaller than a width of knife blade channel 115a, thereby allowing translation of knife blade 193b through knife blade channel 115a.

In operation, when jaw members 110 and 120 are in the second position and grasping tissue therebetween, actuation of the knife trigger assembly 70 causes knife 192 to translate distally. Accordingly, knife base 193a translates through knife base channel 115b while knife blade 193b translates through knife blade channel 115a, thereby cutting tissue disposed between jaw members 110 and 120 along the tissue seal. Knife base 193a is captured within knife base channel 115b and sealing plate 122, since knife base 193a is wider than knife blade channel 115a. Thus, only knife blade 193b extends through knife blade channel 115a. This configuration, namely a cylindrical knife base 193a in a captured, or guided, channel reduces knife splay and allows knife 192 to more easily travel through a designated path. Further, the cylindrical base 193a allows the knife 192 to maintain symmetrical strength while cutting and provides structural support to help keep cutting forces focused in the cutting direction.

Figure 6C:
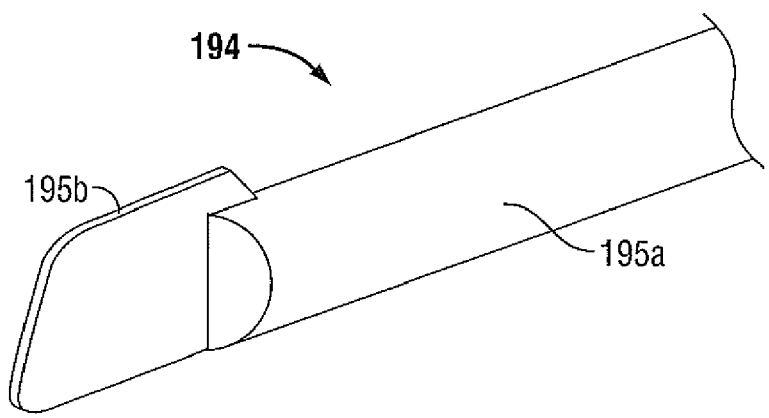
FIG. 6C is a perspective view of a distal end of a knife according to another embodiment of the present disclosure.

Referring now to FIG. 6C, another embodiment of the knife is shown. Similar to knife 192, knife 194 includes a knife base 195a and a knife blade 195b. Knife base 195a is cylindrical in shape, as shown. Knife blade 195b is mounted on a distal end of knife base 195a and extends distally and upwardly from the distal end of knife base 195a. Knife 194 operates in substantially the same manner as knife 192, described above and contains all of the advantages described above in relation to knife 192.

Figure 7A:
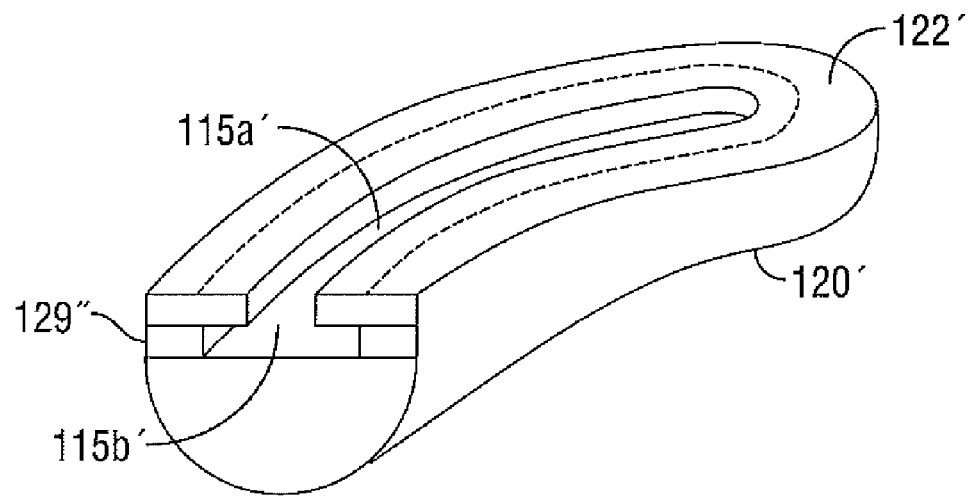
FIG. 7A is a perspective view of one of the jaw members in accordance with one embodiment of the present disclosure.

As shown in FIG. 7A, knife base channel 115b' defined within insulative substrate 129" of jaw member 120' may be configured having a rectangular cross-section defined therein. Jaw member 120' further includes a knife blade channel 115a' having a width "Y'" defined within sealing surface 122' which is in vertical registration with knife base channel 115b'. Knife base channel 115b' has a width "X'", which is greater than width "Y'".

Figure 7B:
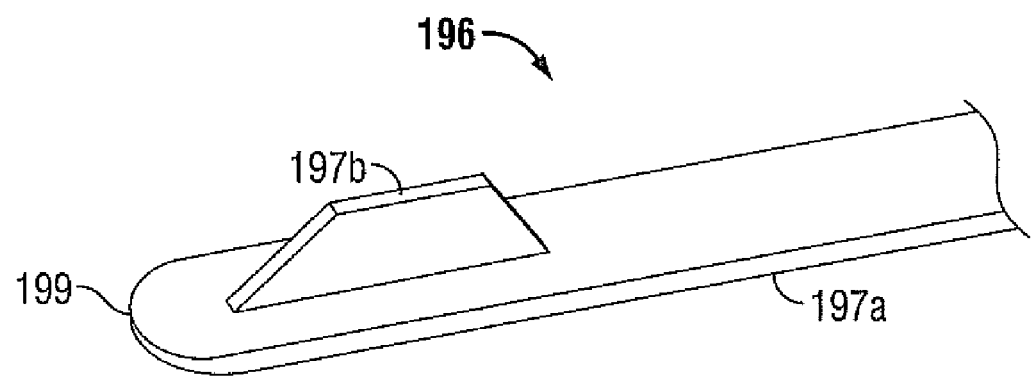
FIG. 7B is a perspective view of a distal end of a knife according to another embodiment of the present disclosure.

Referring now to FIG. 7B, a knife 196, configured for operation with jaw member 120', is shown including knife base 197a having a full radii curved distal tip 199 and knife blade 197b disposed on top of and substantially perpendicular to knife base 197a to form a T-shape. Knife base 197a is substantially similar in cross-sectional shape and slightly smaller than knife base channel 115b, such that knife base 197a may translate through knife base channel 115b'. As described above, an L-shaped knife assembly is contemplated by the present disclosure. Such a cross-sectional shape may be easily formed from a flat stock, and may be more advantageous for curved knife slots by forming v-shaped "cut-outs" in the base portion of the "L".

Upon actuation of knife 196 via knife trigger assembly 70 (see also FIGS. 2A-B), knife base 197a translates distally through knife base channel 115b' as knife blade 197b translates distally through knife blade channel 115a'. Knife base 197a is captured within knife base channel 115b' due to the decreased width of knife blade channel 115a' relative to knife base channel 115b'. Thus, only knife blade 197b translates through knife blade channel 115a' thereby cutting sealed tissue disposed between the jaw members. This captured configuration of knife base 197a adds structural support, allows the knife 196 to more easily translate through a curved path and helps to reduce knife splay.

As illustrated in FIG. 4B, jaw member 110, similar to jaw member 120, includes a support base 119 that extends distally from flange 113 and which is configured to support an insulative substrate 119' thereon. Insulative substrate 119', in turn, is configured to support an electrically conductive tissue engaging surface or sealing plate 112 thereon. Sealing plate 112 may be affixed atop the insulative substrate 119' in any known manner in the art. An outer housing 114 includes a cavity 114a that is dimensioned to securely engage the electrically conductive sealing surface 112 as well as the support base 119 and insulative substrate 119'. Jaw member 110 may also include knife channel 115a defined therein. Knife blade channels 115a of jaw members 110 and 120 may form a single, complete knife blade channel 115a. In other words, the knife blade channel 115a is formed from two knife channel halves, knife blade channel half 115a defined in sealing plate 112 of jaw member 110 and knife blade channel half 115a defined in sealing plate 122 of jaw member 120. It is envisioned that the knife blade channel 115a may be configured as a straight slot with no degree of curvature which, in turn, causes the blade 190 to move through the tissue in a substantially straight fashion. Alternatively and as shown, the knife blade channel 115a may be curved which has certain surgical advantages.

As mentioned above, when the jaw members 110 and 120 are closed about tissue, a complete knife blade channel 115a is formed, thereby allowing longitudinal extension of the knife blade 190 in a distal fashion to sever tissue along a tissue seal. Knife blade channel 115a may be completely disposed in one of the two jaw members, e.g., jaw member 120, depending upon a particular purpose. Further, while the knife base channel 115b is described above as being defined within jaw member 120, it is also contemplated that the configuration of the jaw members may be reversed. For example, jaw member 110 may include a knife blade channel 115a and a knife base channel 115b, for translation of the knife therethrough. In such a configuration, jaw member 120 may also include a knife blade channel 115a, or the knife channel 115a may be completely disposed within jaw member 110.

From the foregoing and with reference to the various figure drawings, those skilled in the art will appreciate that certain modifications can also be made to the present disclosure without departing from the scope of the same. For example, the teachings of the present disclosure may be associated with an open forceps, such as one having a scissor-type configuration. Such a forceps may include two shaft members pivotable around a common pivot.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
    an end effector assembly having first and second jaw members disposed in opposed relation and moveable from a first, open position to a second, closed position for grasping tissue therebetween, wherein the jaw members include knife blade channels defined therein and wherein at least one of the knife blade channels includes a knife base portion and a knife edge portion, the knife base portion having an enclosed polygonal longitudinal cross-section defined within one of the first and second jaw members that opens toward the knife edge portion; and
    a knife including a knife edge and a knife base, the knife base including a top surface, a bottom surface, and a polygonal longitudinal cross-section corresponding to the polygonal longitudinal cross-section of the knife base portion of the at least one knife blade channel, wherein the knife is configured to translate through the knife blade channels and the top and bottom surfaces of the knife base are configured to slidingly engage surfaces of the jaw member that define the knife base portion of the at least one knife blade channel upon translation of the knife through the knife blade channels.

2. The forceps according to claim 1, wherein the knife base portion captures the knife base therein to prevent the knife from escaping the knife blade channel upon distal translation thereof.

3. The forceps according to claim 1, wherein at least one of the jaw members is adapted to connect to an electrosurgical energy source to communicate energy to tissue disposed between the jaw members.

4. The forceps according to claim 1, wherein distal portions of the knife blade channels are curved.

5. The forceps according to claim 4, wherein the jaw members are curved.

6. The forceps according to claim 1, wherein the knife base portion of the at least one knife blade channel defines a rectangular cross-section and the knife base defines a corresponding rectangular cross-section.

7. The forceps according to claim 1, wherein the knife base includes a full radii curved distal tip.

8. The forceps according to claim 1, wherein the knife edge is disposed substantially perpendicular to the knife base.

9. The forceps according to claim 1, wherein a portion of at least one knife blade channel is dimensioned to have a width that is less than the width of the remaining knife blade channel to secure and retain the knife base therein.

10. The forceps according to claim 1, wherein the knife edge is disposed in vertical registration with the knife base.

11. A forceps, comprising:
a housing having a shaft extending therefrom, the shaft having an end effector assembly disposed at a distal end thereof, wherein the end effector assembly defines a longitudinal axis therethrough and includes:
first and second jaw members disposed in opposed relation and moveable from a first, open position to a second, closed position for grasping tissue therebetween, wherein the jaw members include knife blade channels defined therein and wherein at least one of the knife blade channels includes a knife base portion and a knife edge portion that define a T-shaped or an L-shaped longitudinal cross-section, wherein the knife base portion is enclosed within one of the first and second jaw members and opens toward the knife edge portion; and
a knife including a knife edge and a knife base, the knife base including a top surface, a bottom surface, and a T-shaped or L-shaped longitudinal cross-section corresponding to the T shaped or L-shaped longitudinal cross-section of the knife base portion of the at least one knife blade channel, wherein the knife is configured to translate through the knife blade channels and the top and bottom surfaces of the knife base are configured to slidingly engage surfaces of the jaw member that define the knife base portion of the at least one knife blade channel upon translation of the knife through the knife blade channels.

12. The forceps according to claim 11, wherein the knife base portion captures the knife base therein to prevent the knife from escaping the knife blade channel upon distal translation thereof.

13. The forceps according to claim 11, wherein at least one of the jaw members is adapted to connect to an electrosurgical energy source to communicate energy to tissue disposed between the jaw members.

14. The forceps according to claim 11, wherein distal portions of the knife blade channels are curved.

15. The forceps according to claim 14, wherein the jaw members are curved.

16. The forceps according to claim 11, wherein the knife edge is disposed substantially perpendicular to the knife base.

17. The forceps according to claim 11, wherein a portion of at least one knife blade channel is dimensioned to have a width that is less than the width of the remaining knife blade channel to secure and retain the knife base therein.

18. The forceps according to claim 11, wherein the knife edge is disposed vertical registration with the knife base.

* * * * *